(12) United States Patent
Siljander et al.

(10) Patent No.: US 7,892,528 B2
(45) Date of Patent: Feb. 22, 2011

(54) CONTROLLING BEDBUGS WITH SYNTHETIC PHEROMONES AND/OR INFRARED RADIATION

(76) Inventors: Eric D. Siljander, #5 - 1184 Inlet St., Coquitlam, British Columbia (CA) V3B 6E4; Stephen Takács, 1001 Richards Street, #2008, Vancouver, British Columbia (CA) V6B 1J6; Regine Gries, 484 Cariboo Crescent, Coquitlam, B.C. (CA) V3C 4X7; Gerhard Gries, 484 Cariboo Crescent, Coquitlam, B.C. (CA) V3C 4X7

( * ) Notice: Subject to any disclaimer, the term of this patent is extended or adjusted under 35 U.S.C. 154(b) by 792 days.

(21) Appl. No.: 11/622,575

(22) Filed: Jan. 12, 2007

(65) Prior Publication Data
US 2008/0168703 A1 Jul. 17, 2008

(51) Int. Cl.
*A01N 25/00* (2006.01)
(52) U.S. Cl. ......................................................... 424/84
(58) Field of Classification Search ........................ None
See application file for complete search history.

(56) References Cited

U.S. PATENT DOCUMENTS

| | | | |
|---|---|---|---|
| 2,059,835 | A | 11/1936 | Worthing et al. |
| 2,330,034 | A | 9/1943 | Doodchenko |
| 4,817,329 | A | 4/1989 | Forbes |
| 4,843,752 | A | 7/1989 | Munemasa et al. |
| 4,961,283 | A | 10/1990 | Forbes |
| 5,528,049 | A | 6/1996 | Callahan |
| 5,572,825 | A | 11/1996 | Gehret |
| 5,915,949 | A | 6/1999 | Johnson |
| 6,792,713 | B2 | 9/2004 | Snell |
| 2005/0091911 | A1 | 5/2005 | Matts et al. |
| 2006/0150470 | A1 | 7/2006 | Ronnau |
| 2006/0261188 | A1 | 11/2006 | Ito et al. |
| 2007/0044372 | A1 | 3/2007 | Lang et al. |

FOREIGN PATENT DOCUMENTS

| | | |
|---|---|---|
| WO | 2005/096824 A | 10/2005 |
| WO | WO 2006/121346 | 11/2006 |
| WO | 2007/027601 A | 3/2007 |
| WO | 2008/051501 A | 5/2008 |

OTHER PUBLICATIONS

H. Schmitz, S. Trenner, M.H. Hoffmann & H. Bleckmann, "The ability of *Rhodnius prolixus*(Hemiptera; Reduviidae) to approach a thermal source solely by its infrared radiation." J. Insect Physiol., vol. 46, 2000, pp. 745-751, XP002499561 cited in the application p. 745, col. 1, paragraph 1; figure 1 p. 749, col. 2, paragraph 1-p. 750, col. 1, paragraph 2.

H.Z. Levinson, A.R Levinson, B. Muller & R.A. Steinbrecht: "Structure of sensilla, olfactory perception, and behaviour of the bedbug, *Cimex lectularious*, in response to its alarm pheromone." J. Insect Physiol., vol. 20, 1974, pp. 1231-1248, XP002499406 cited in the application p. 1231, paragraph 1—p. 1232, paragraph 1 p. 1242, paragraph 2 p. 1243, paragraph 3—p. 1246, paragraph 2.

B.D. Parashar et al.: "Aggregation activity induced by the excreta extracts in *Cimex lectularius* (Hemiptera: Cimicidae)." Entomon, vol. 28, No. 3, 2003, pp. 215-222, XP009106949 p. 216, paragraph 2 figure 1; tables 1,2 p. 220, paragraph 2-p. 221, paragraph 2.

E. Siljander, D. Penman, H. Harlan & G. Gries: "Evidence for male- and juvenile specific contgact pheromones of the common bed bug *Cimex lectularius*." Entomol. Experim. Applic, vol. 125, Oct. 2007, pp. 215-219, XP002499407 p. 215, col. 2, paragraph 2 'Discussion'.

International Search Report and Written Opinion dated Oct. 28, 2008, Appl. No. PCT/US2007/026046.

H. Schmitz, et al., The ability of *Rhodnius prolixus* (Hemiptera; Reduviidae) to approach a thermal source solely by its infrared radiation. 46 Journal of Insect Physiology 745-751 (2000).

C.G. Johnson, The ecology of the bed-bug, *Cimex lectularius* L., in Britain. 41 Journal of Hygiene 345-461 (1942).

H. Levinson, Assembling and alerting scents produced by the bedbug, *Cimex lectularius* 27 L. Experientia 102-103 (1971).

H. Levinson, et al., Action and composition of the alarm pheromone of the bedbug *Cimex lectularius* 61 L. Naturwissenschaften 684-685 (1974).

H. Levinson, et al. Structure of sensilla, olfactory perception, and behaviour of the bedbug, *Cimex lectularius*, in response to its alarm pheromone. 20 Journal of Insect Physiology 1231-1248 (1974).

K. Mellanby, The physiology and activity of the bed-bug (*Cimex lectularlus* L) in a natural infestation. 31 Parasitology 200-211 (1939).

C. Montes, et al. Maintenance of a laboratory colony of *Cimex lectularius* (Hemiptera: Cimicidae) using an artificial feeding technique. 39 Journal of Medical Entomology 675-679 (2002).

*Primary Examiner*—Johann R Richter
*Assistant Examiner*—Frank I Choi

(57) ABSTRACT

Disclosed are methods for attracting and thereby controlling bedbugs. One volatizes a synthetic pheromone and generates infrared radiation adjacent the location and exposes bedbugs thereto. The pheromone volatizer and/or radiation generator are preferably incorporated into traps, bait stations and monitoring stations.

15 Claims, 10 Drawing Sheets

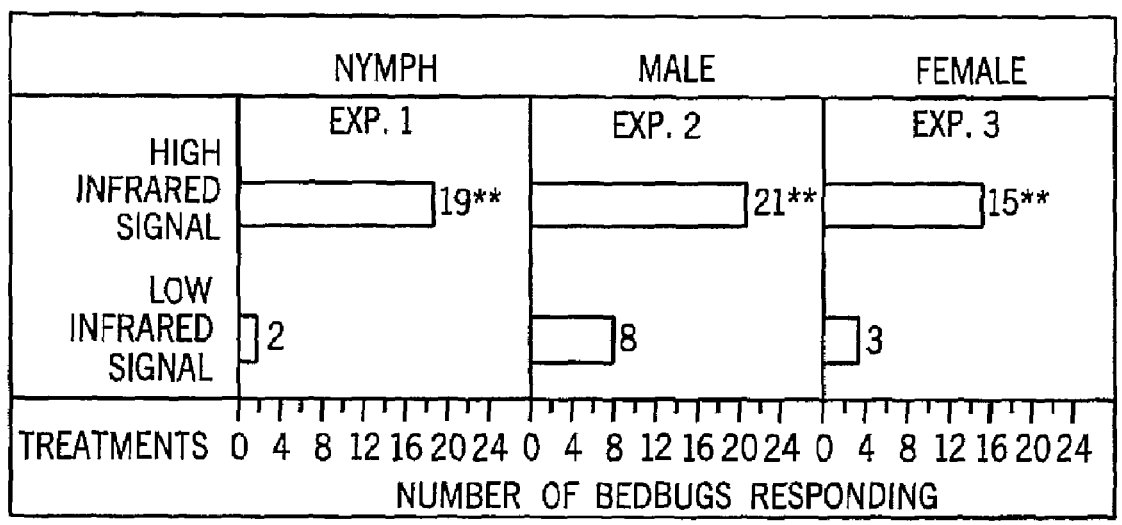
FIG. 3
FIG. 4
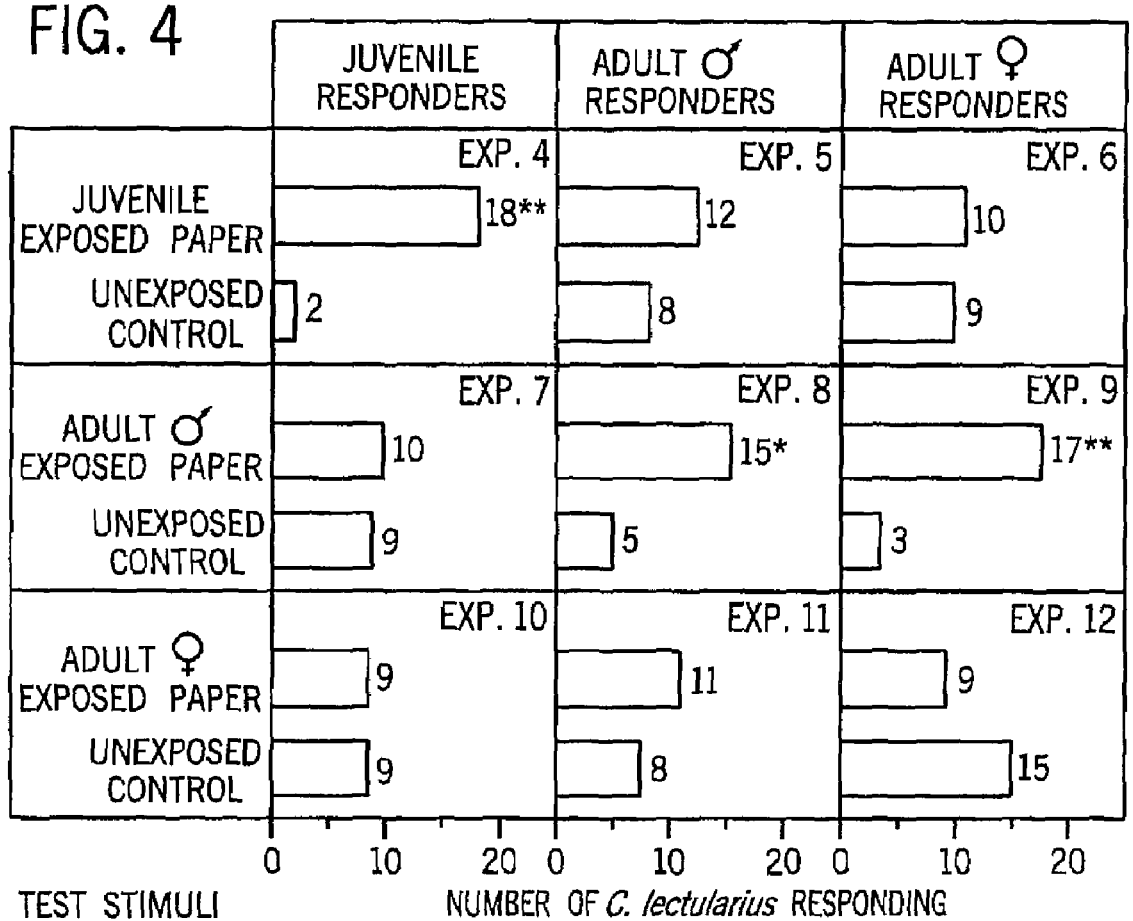

CONTROLLING BEDBUGS WITH SYNTHETIC PHEROMONES AND/OR INFRARED RADIATION

CROSS-REFERENCE TO RELATED APPLICATIONS

Not applicable.

STATEMENT REGARDING FEDERALLY SPONSORED RESEARCH/DEVELOPMENT

Not applicable

BACKGROUND OF THE INVENTION

The present invention relates to the use of pheromones and/or infrared radiation for attracting bedbugs. These attractants can be associated with devices for monitoring or detecting infestations, or devices for trapping bedbug populations.

There have been attempts to control bedbug infestation through applications of insecticidal chemicals to infected areas and materials (especially mattresses). This approach has some drawbacks. For example, it can expose those using a treated area or mattress too soon after application to odor or other undesired characteristics of the pesticidal chemical. Further, unless the chemicals are used regularly, without regard to whether an infestation is known to already exist (which procedure will significantly increase costs), those sleeping in an infected area can be bitten before one knows to begin treatment.

Bedbugs feed on human blood. Thus, they are not merely unsightly, they leave ugly skin markings. However problematic this is for residential bedrooms, it is an even more serious problem for motels and the like. With respect to such commercial bedrooms there is more opportunity for external infection sources to bring bedbugs to the site, and should there be an unknown infestation which causes biting of customers before it is dealt with, there is a severe risk of customer dissatisfaction and adverse publicity, likely leading to a long term significant reputation loss.

There have been a number of publications regarding various characteristic of bedbugs. See generally C. Johnson, The ecology of the bed-bug, *Cimex lectularius* L., 41 Journal of Hygiene 345-461 (1942); H. Levinson et al., Assembling and alerting scents produced by the bedbug, *Cimex lectularius* L., 27 Experientia: 102-103 (1971); H. Levinson et al., Action and composition of the alarm pheromone of the bedbug *Cimex lectularius* L., 61 Naturwissenschaften 684-685 (1974); H. Levinson et al., Structure of sensilla, olfactory perception, and behaviour of the bedbug, *Cimex lectularius*, in response to its alarm pheromone, 20 Journal of Insect Physiology 1231-1248 (1974); K. Mellanby, The physiology and activity of the bed-bug (*Cimex lectularius*) in a natural infestation, 31 Parasitology 200-211 (1939); and H. Schmitz et al., The ability of *Rhodnius prolixus* (Hemiptera; Reduviidae) to approach a thermal source solely by its infrared radiation, 46 Journal of Insect Physiology 745-751 (2000).

Unrelated to bedbugs, there have been attempts to rely on attractants to lure certain other types of insects to a trap or the like. See generally U.S. Pat. No. 5,572,825 (certain pheromones used to attract bedbugs to a trap) and WO 2006/121346 (infrared used to lure mosquitoes to a trap). See also U.S. Pat. Nos. 5,528,049 and 6,792,713, and also U.S. patent application publication 2005/0091911.

See also H. Schmitz et al., The ability of *Rhodnius prolixus* (Hemiptera; Reduviidae) to approach a thermal source solely by its infrared radiation, 46 Journal of Insect Physiology 745-751 (2000).

Notwithstanding these developments, it is desired to develop ways to attract (and thereafter control) bedbug populations, particularly where these techniques do not require the use of pesticidal chemicals.

BRIEF SUMMARY OF THE INVENTION

It has been discovered that bedbug pheromones exist which can attract bedbugs when volatized from an insect control device, and that these pheromones have a discrete group of essential components which when blended together can be used to attract bedbugs. Infrared radiation can assist in attracting bedbugs to the specified location as well.

The invention provides a chemical formulation (separate from a bedbug) which is capable of attracting bedbugs when volatized. The formulation has a monoterpene, a saturated aldehyde, an unsaturated aldehyde, and a ketone (preferably two monoterpenes, two saturated aldehydes, three unsaturated aldehydes, one aromatic aldehyde, one aromatic alcohol, and a ketone). Preferably there is also an acetate. Most preferably there is nonanal, decanal, (E)-2-hexenal, (E)-2-octenal, (E,E)-2,4-octadienal, benzaldehyde, benzyl alcohol, (+)-limonene, (−)-limonene and sulcatone.

One can volatize the chemical formulation form a bedbug control device adjacent a location. A bedbug will as a result be attracted towards that specified location. The bedbug can be male or female, adult or nymph, virgin or mated. Preferably the bedbug is a common bedbug, *Cimex lectularius*.

A bedbug control device may be selected from the group consisting of traps, baiting stations containing a chemical toxic to bedbugs, and bedbug indicator stations. Where a toxin is used, the exact toxin is not critical, and in any event can be an appropriate conventional toxin of the type optimized for the specific bedbug population of interest (e.g. pyrethrins (cyfluthrin, permethrin) or carbamates (bendiocarb).

Such a device may be designed to retain the bedbugs that have been attracted and killed. Alternatively, the device may be designed so that the bedbug feeds on or otherwise contacts a slow-acting poison, regardless of whether the poisoned bedbug remains in the device after being poisoned. For example, the toxin could be slow-acting and be of a type that causes the bedbug to contaminate its normal harborage after it leaves the device. This might even facilitate control of the remainder of the population who do not visit the device.

Alternatively, the device may be for purposes of monitoring whether an infestation exists in a building or other area, rather than by itself completely controlling the infestation. For example, a commercial pest control company might place such a device in a room. Then, after a day or so has passed, the device could be checked to see if any bedbugs are in it.

If bedbugs are found, a further more aggressive bedbug control treatment could be implemented (e.g. a general spraying). If no bedbugs were found, no further treatment would be provided in that area.

The infrared radiation can be generated from a heat source such as an electric bulb or from a light emitting diode. The infrared radiation can preferably be comprised of at least one wavelength between 0.7 and 12 μm (e.g. between 0.7 and 2 μm. Optionally, one can reflect the radiation without the heat into the environment where bedbugs may be.

Another aspect of the invention provides a bedbug control apparatus. There is a housing, an infrared generator, and/or the above chemical formulation, positioned adjacent to or in the housing, and at least one way for the bedbug to access the housing. The apparatus may be in the form of a trap having openings which enable bedbugs to easily enter the trap, yet have difficulty leaving (e.g. a tapered opening). In addition to the use of infrared and a volatile pheromone one could also include in the trap another chemical attractant, such as a contact pheromone.

A sticky or glue surface may act as the trapping mechanism. It may instead be a baiting station that contains a toxic agent to kill entering bedbugs (and/or optionally other insects as well). Thus, regardless of whether there is trapping or toxic capability, or even monitoring capability, having such a device at one position can keep bedbugs away from another (e.g. a mattress/bed).

It will be appreciated that the present invention provides improved methods for controlling bedbugs, devices for practicing these methods, and desirable chemical bedbug attractants for use therewith. Contrary to the normal desire to avoid bedbugs, here an attractant approach is used for their control.

The invention is particularly well suited for use in residential environments. It permits luring of bedbugs at significant distances from the device, and thus a single device is likely to be sufficient for bedroom protection. Further, such devices are likely to be capable of operating at low cost. Most importantly they can help control bedbugs without requiring a general spay treatment of toxic pesticides around and on mattresses and bedding.

The foregoing and other advantages of the present invention will be apparent from the following description. In the description that follows, reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

BRIEF DESCRIPTION OF THE DRAWINGS

FIG. 3 graphically illustrates the relative rate of attraction between high and low infrared signal radiation stimuli;

FIG. 4 graphically illustrates the response of bedbugs in still-air olfactometers to paper discs previously exposed for 6 days to 10 juveniles (experiments 4-6), 10 males (experiment 7-9) or 10 females (experiments 10-12). These experiments indicate that juvenile and male bedbugs generated a contact pheromone affecting arrestment;

DETAILED DESCRIPTION OF THE INVENTION

We have identified pheromone components, and pheromone formulations capable of attracting common bedbugs. One has ten volatile components [nonanal, decanal, (E)-2-hexenal, (E)-2-octenal, (E,E)-2,4-octadienal, benzaldehyde, benzyl alcohol, (+)-limonene, (−)-limonene, sulcatone]. A synthetic formulation of these components attracted bedbugs.

Our experiments also showed that common bedbugs are attracted to infrared radiation. For example, this worked with infrared radiation emanating from a heat source (42° C.) that was ≧1 m away from test insects.

We propose to deploy such a synthetic pheromone formulation or such infrared radiation, or a combination thereof, with an insect control device. For example, a trap could attract and capture bedbugs. This could be placed in any room to (i) detect the presence of bedbugs, (ii) divert them from other attractive sources such as sleeping humans, (iii) help reduce an existing bedbug infestation, or (iv) monitor attempted eradication of such infestation by insecticide applications.

A. Response to Infrared Radiation.

Figure 1:
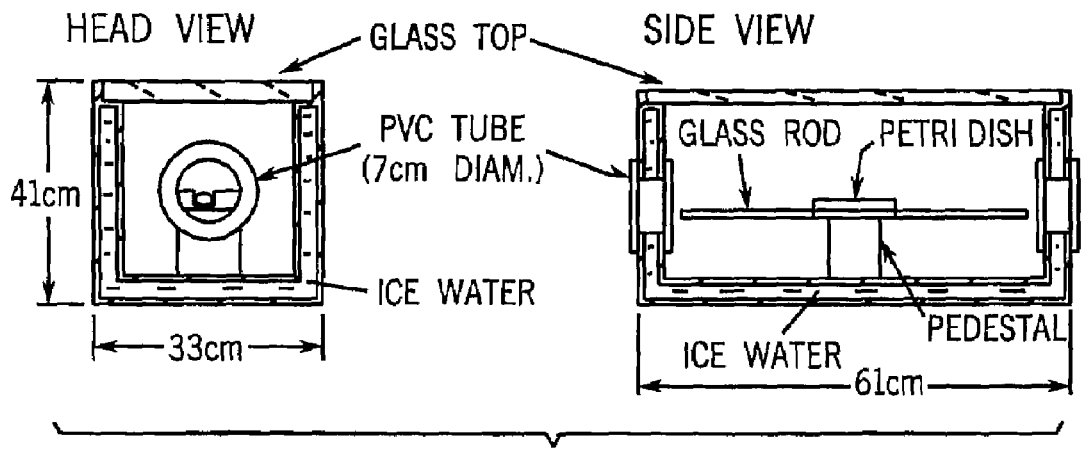
FIG. 1 illustrates head and side views of an apparatus for bioassaying behavioral responses of bedbugs to infrared radiation.

Attraction responses of *C. lectularius* bedbugs to infrared radiation were tested in a cooled chamber designed to eliminate external thermal cues (FIG. 1). The chamber consisted of a bioassay aquarium (50.5×26.7×33 cm high) nested inside a larger aquarium (61×33×41 cm high) with ice water between them, and a glass top covering the bioassay aquarium. The air temperature within the bioassay aquarium (10° C.+/−1° C.) and the water temperature (4.0° C.+/−0.5° C.) were monitored continuously. A PVC tube (7 cm diam) in each of the two head sections of the chamber (FIG. 1) allowed infrared radiation to enter the bioassay aquarium.

Bedbugs were released from an etched open Petri dish (10 cm diam) resting on a pedestal (9×9×10 cm) within the bioassay aquarium (FIG. 1). They responded to infrared radiation entering the chamber through the PVC tubes by climbing onto and walking toward the distal end of an etched glass rod (0.8×45 cm) inserted through the Petri dish.

Figure 2:
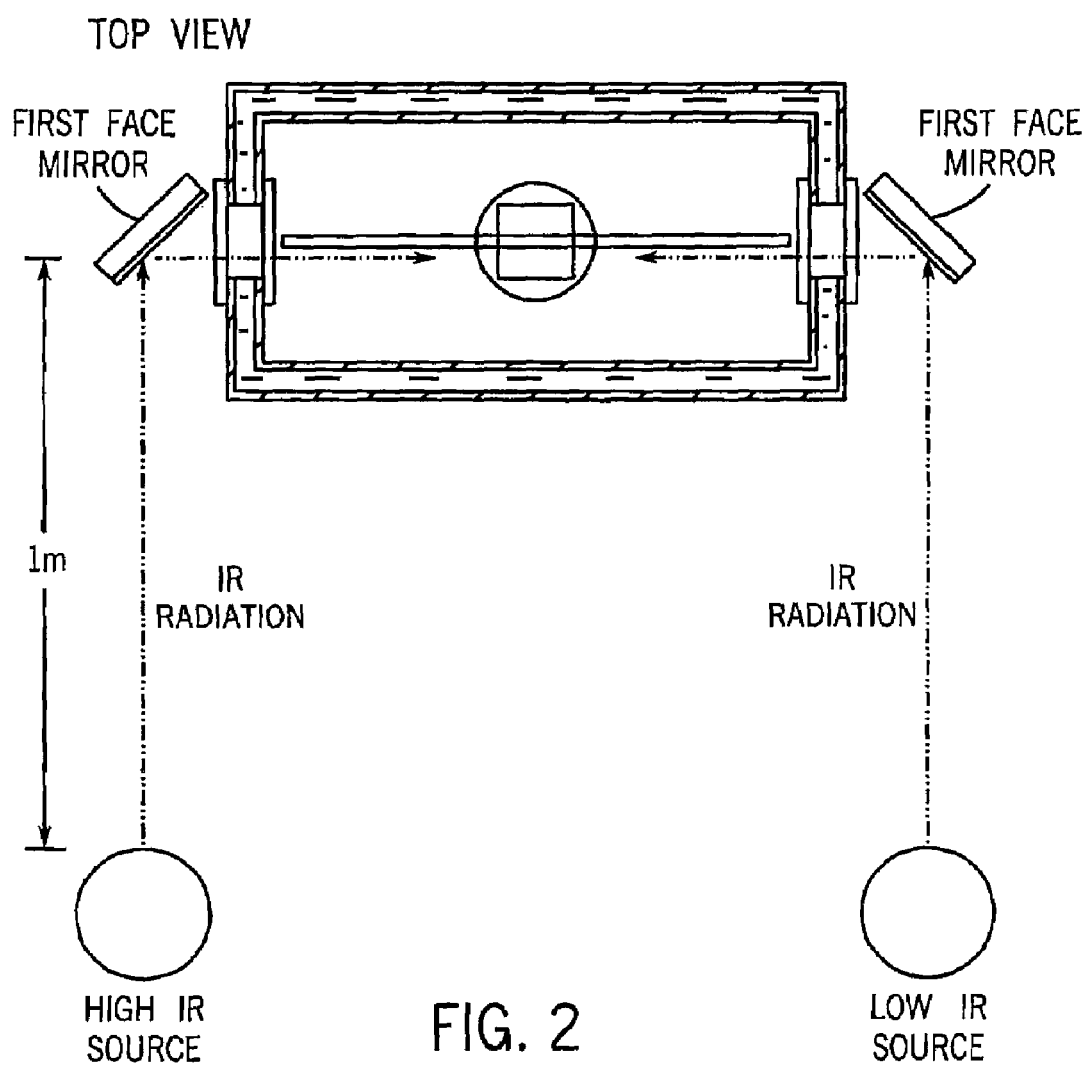
FIG. 2 schematically illustrates exposing bedbugs to different types of infrared radiation.

High and low infrared radiation was generated from Pyrex glass flasks (1000 ml) containing heated (42° C.) or ice-cooled (4° C.) water (FIG. 2), respectively. Front-surface optical mirrors (13×13 cm) reflected infrared radiation (but not heat) into the bioassay aquarium. To ensure that infrared radiation stimuli could be perceived by bedbugs while they were residing in the Petri dish or walking on the glass rod, a horizontal laser was used to properly position both infrared sources and mirrors. A thermographic camera (AGEMA Thermovision 550), sensitive in the wavelength range of 3-5 μm and able to resolve temperature difference of 0.1° C., confirmed the apparent temperature of respectively 32+/−2° C. and 6+/−2° C. that was reflected by the mirrors.

Bedbugs were kept singly in a Petri dish, and were allowed to acclimate for 2-6 hours at room temperature in darkness. For each experimental replicate, a single insect was then placed into the Petri dish within the bioassay aquarium. Individuals that mounted the rod and walked to one distal end within 1-30 minutes were classed as responders and were included in statistical analyses. Bedbugs that did reach the distal end of a glass rod already within 60 seconds (=panic responders due to handling) or not at all within 30 min (=non-responders) were not included in statistical analysis. Replicates of all experiments were conducted under red light to facilitate recording of the insects' behavioral response. As shown in FIG. 3, high infrared was a preferred attractant.

B. Response to Contact Pheromones.

Paper towel discs (9 cm diam. folded eight times for corrugation) were exposed in Petri dishes (9×5 cm) for six days to 10 juvenile, 10 male, or 10 female bedbugs at room temperature under a 16L: 8D photoperiod. Such discs received 1440 contact pheromone hour equivalents (1 CPHE=contact pheromone deposited by one bedbug during one hour). To extract the contact pheromone, filter papers (Whatman no. 1) exposed to juveniles (100 insects on one 9-cm diam. paper or 125 insects on five 5.5-cm diam papers) were washed with methanol for ~30 min at room temperature. The supernatant was withdrawn with a pipette and stored at room temperature.

Responses to test stimuli were bioassayed in still-air (instead of moving air) olfactometers because bedbugs inhabit enclosed microhabitats with little or no air movement. The olfactometers consisted of three glass chambers (each 3.5×10 cm ID) linearly interconnected by glass tubes (each 2.5×1 cm ID). Test stimuli were randomly assigned to one of the two lateral chambers, each containing a paper towel disc (9 cm diam.; folded eight times for corrugation) with a tab to facilitate inter-chamber movement of bioassay insects. Stimuli were pipetted onto the discs, with treatment and control discs receiving the same amount of solvent. For each replicate, one bedbug was released in the central chamber of the olfactometer three hours before the end of scotophase, when bedbugs are most active. An insect was classed as a responder when it was found 16-18 hours later on a paper disc or within a lateral glass tube in a state of akinesis. All experiments were conducted at 22-24° C., 25-40% R.H., under a 3D: 13L photoperiod.

Experiments 4-12/FIG. 4 tested the response of juveniles, males and females to paper exposed to 4th-5th instar juveniles (experiments 4-6), adult males (experiments 7-9), or adult females (experiments 10-12).

Figure 5:
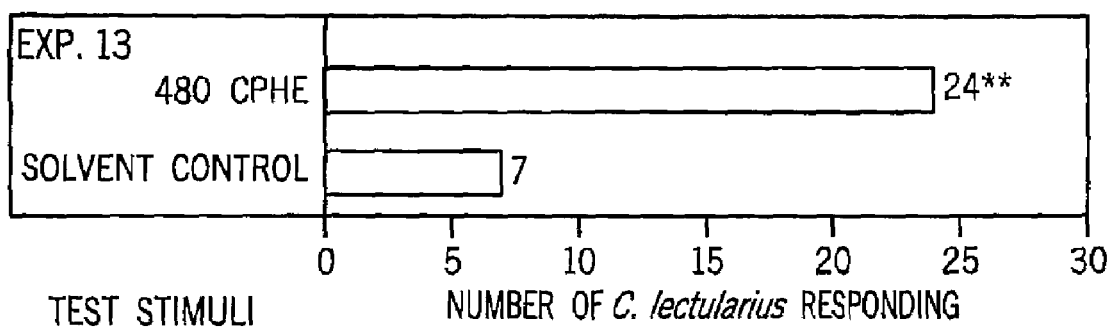
FIG. 5 graphically illustrates the response of juvenile bedbugs in still-air olfactometers to a methanol extract of paper exposed to juvenile conspecifics.
Figure 7:
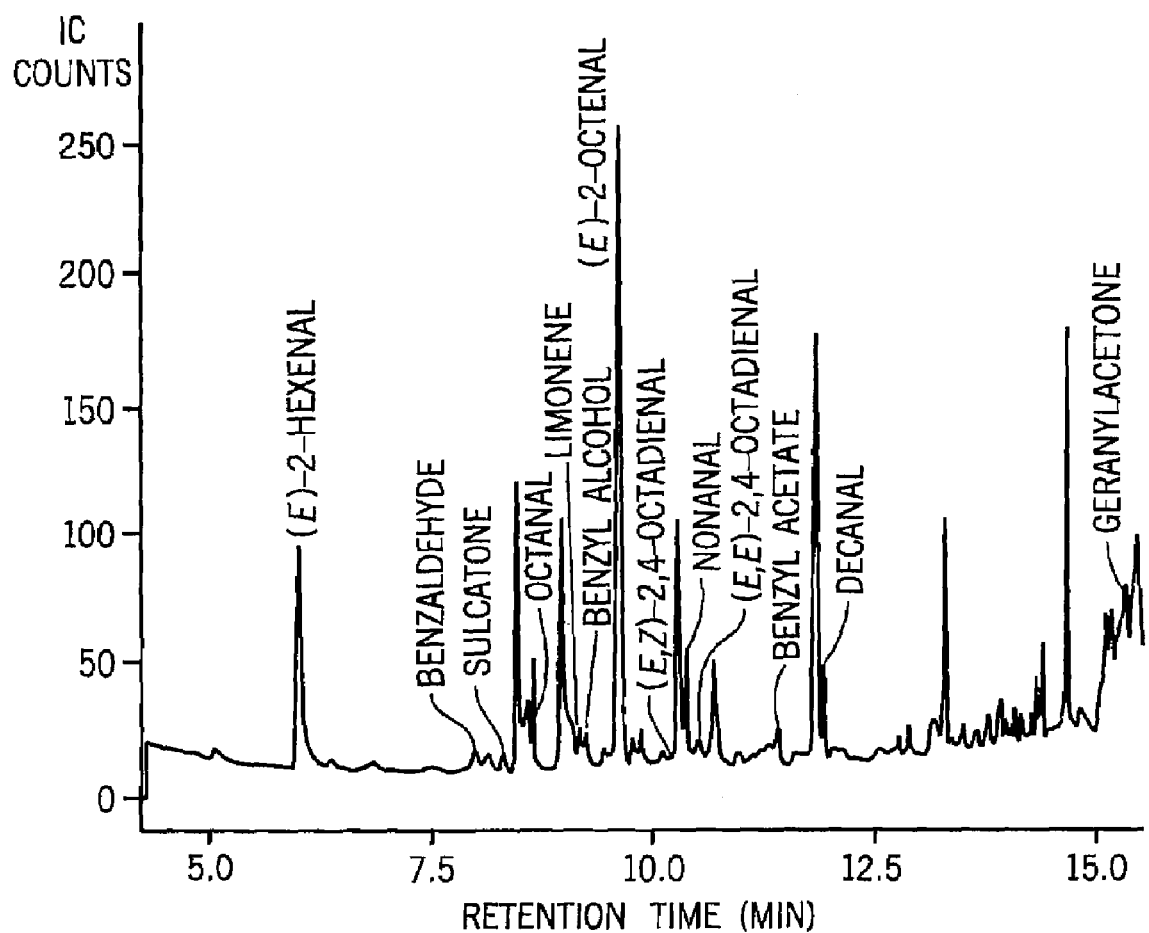
FIG. 7 is a representative aliquot gas chromatogram of Porapak Q bedbug jar aeration extract (JAE). Chromatography: Varian Saturn 2000 Ion Trap GC-MS fitted with a DB-5 column (30 m×0.25 mm ID). Temperature program: 50° C. (2 min), 10° C. per min to 280° C.

In experiment 13/FIG. 5, a methanol extract of juvenile-exposed paper was tested at 480 CPHE to determine whether it elicited a behavioural response comparable to exposed paper. Numbers of bedbugs responding to treatment and control stimuli in still-air olfactometer experiments 4-13 were analyzed with the $\chi^2$ goodness-of-fit test, using Yates correction for continuity ($\alpha$=0.05).

In olfactometer experiments 4-12, bedbugs preferred paper discs that had been exposed to conspecifics. This preference appears somewhat stage-specific. Juveniles but not males or females preferred juvenile-exposed paper over unexposed control discs (FIG. 4, experiments 4-6). Unlike juveniles, males and females preferred male-exposed paper discs over control discs (FIG. 4, experiments 7-9). Female-exposed paper discs were not attractive to juveniles, males or females (FIG. 4, experiments 10-12). Methanol extract of paper exposed to juveniles tested at ~480 CPHE elicited a significant behavioral response from juvenile conspecifics (FIG. 5, experiment 13).

As shown in FIG. 5, there was a response of juvenile bedbugs in still-air olfactometer experiment 13 to methanol extract of paper exposed to juvenile conspecifics. 1 CPHE=contact pheromone hour equivalent=contact pheromone deposited by one bedbug during 1 hour. Number of insects responding to each stimulus is given next to bars. Aliquots of 480 CPHE were tested; the same amount of methanol (95 μl) was applied to treatment and control stimuli.

C. Identification of a Complex Airborne Pheromone Formulation.

To acquire airborne pheromone, colony jars containing ~500-700 bedbugs of mixed stage and sex were placed in a cylindrical Pyrex glass chamber (15.5×20 cm). An electrical pump drew charcoal-filtered air at ~2 l/min through each chamber and through a glass column (14×1.3 cm OD) containing Porapak Q (50-80 mesh; Waters Associates, Inc., Milford, Mass., USA). After 72 hours, volatiles were eluted from the Porapak Q trap with 2 ml of pentane. These jar aeration extracts (JAEs) contained ~43,200 bug hour equivalents (1 BHBE=volatiles released by one *C. lectularius* during one hour), and were stored under darkness at −15° C.

JAEs were analyzed by coupled gas chromatography—mass spectrometry (GC-MS) in full-scan electron impact mode, using a Varian Saturn 2000 Ion Trap GC-MS fitted with a DB-5 column (30 m×0.25 mm ID, J&W Scientific, Folsom, Calif., USA). The temperature program started at 50° C. for 2 min, and then increased at a rate of 10° C. per min to 280° C. Candidate pheromone components were identified by their mass spectra, retention index calculations and comparison with authentic standards.

Aliquots of JAE were concentrated under a nitrogen stream and fractionated through silica gel (0.5 g) in a glass column (14×0.5 cm ID). After pre-rinsing the silica with pentane, JAE aliquots were applied, allowed to impregnate the silica, and then eluted with five consecutive rinses (2 ml each) of pentane/ether, with increasing proportion of ether, as follows: (1) 100:0; (2) 90:10; (3) 75:25; (4) 50:50; (5) 0:100. This procedure generated five fractions containing analytes of increasing polarity.

Responses of bedbugs to test stimuli were bioassayed in still-air olfactometers (as above). Experiments 14-53 were conducted with olfactometers stacked (three rows×three columns) inside yellow plastic bins (38×31×11 cm) to minimize the adverse effects of moving air and directional lighting on the insects' response. To most rigorously compare the attractiveness of test stimuli, experiments were often run in parallel over time, so on any given day a response was recorded for each stimulus.

To determine whether the JAE was attractive, experiment 14 tested the response of juveniles to JAE at ~200 BHE. Considering the attractiveness of JAE in this experiment, and to determine the essential components, parallel experiments 15-20 tested the complete formulation of all five JAE silica fractions combined vs. formulations lacking single fractions. Based on results of experiments 15-20 and those of GC-MS analyses, experiments 21-24 tested a synthetic formulation (SB) of 14 candidate pheromone components [octanal, nonanal, decanal, (E)-2-hexenal, (E)-2-octenal, (E,E)-2,4-octadienal, (E,Z)-2,4-octadienal, benzaldehyde, benzyl alcohol, benzyl acetate, (+)-limonene, (−)-limonene, sulcatone, geranylacetone] at ~200 BHE for its ability to attract juveniles, males, and mated and virgin females.

To identify the most important components, parallel experiments 25-31 tested SB vs. formulations lacking groups of organic molecules, such as monoterpenes (experiment 26), benzyl-group containing compounds (experiment 27), ketones (experiment 28), saturated aldehydes (experiment 29), monoene-aldehydes (experiment 30), or diene-aldehydes (experiment 31). Similarly, parallel experiments 32-45 tested SB vs. formulations lacking a single component. (E,E)-2,4-Octadienal could not be removed as a single component because it kept forming as a rearrangement product of (E,Z)-2,4-octadienal and therefore could not be sufficiently separated by high-performance liquid chromatography. Considering the results of experiments 32-45, experiments 46-53 tested a new synthetic formulation (NSB) [SB minus octanal] vs. formulations lacking one, two or all of the following three components: (E,Z)-2,4-octadienal, benzyl acetate, geranylacetone.

In experiment 54, the ability of the 14-component synthetic formulation (SB) to attract or arrest bedbugs was tested in Plexiglas cage (30×30×42 cm) olfactometers, with four mesh-covered holes (18 cm diam.) for ventilation and a sliding door (21×25 cm) for access. The rough (sandpaper-treated) cage floor allowed the insects to walk easily to either of two paper disc shelters (6 cm diam.; folded six times for corrugation) in opposing corners of the cage. The treatment stimulus (10 SB at ~2000 BHE) and solvent control stimulus were randomly assigned and pipetted onto these discs, with treatment and control discs receiving the same amount of solvent. For each replicate, 10 juvenile bedbugs were released in the center of the cage three hours before the end of scotophase and the number of juveniles on each disc was recorded 16-18 hours later. An insect was classed as a responder when it was found on a paper disc in a state of akinesis. All experiments were conducted at 22-24° C., 25-40% R.H., under a 3D: 13L photoperiod.

Follow-up experiment 55 tested whether the significant response by insects to airborne pheromone in experiment 54 could be enhanced by adding methanol extract of juvenile contact pheromone at 720 CPHE to both treatment and control discs.

Numbers of bedbugs responding to treatment and control stimuli in laboratory still-air olfactometer experiments 14-53 were analyzed with the $\chi 2$ goodness-of-fit test, using Yates correction for continuity ($\alpha=0.05$). The mean proportion of juvenile bedbugs responding to treatment and control stimuli in cage olfactometer experiments 54 and 55 were analyzed with the Wilcoxon rank sum test ($\alpha=0.05$).

Figure 6:
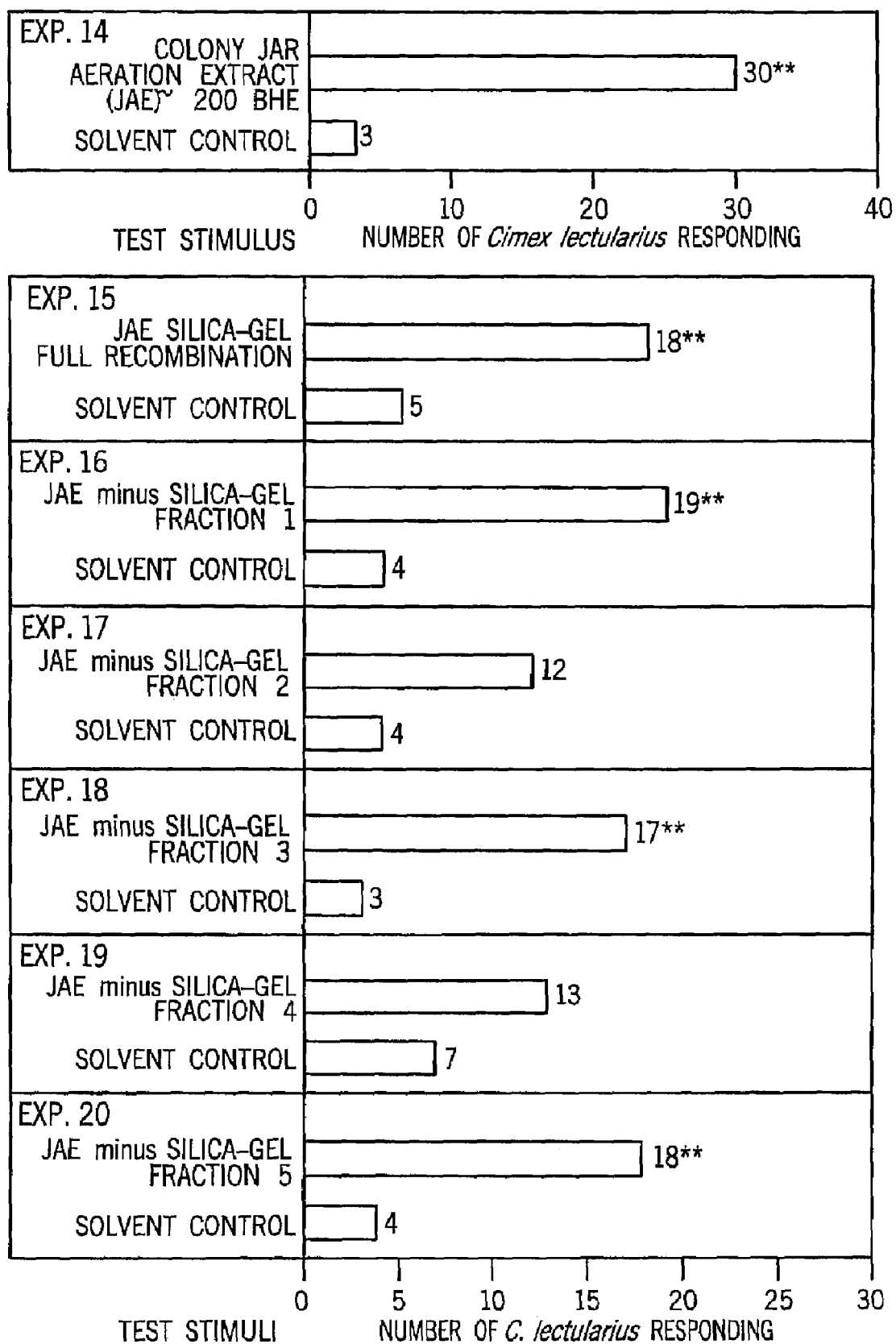
FIG. 6 graphically illustrates the response of juvenile bedbugs in still-air olfactometers to jar aeration extract (JAE) (experiment 14), or to JAE blends lacking one of five silica gel fractions (experiments 15-20)

In sum, Porapak Q jar aeration extracts (JAEs) tested at ~200 BHE attracted juveniles (FIG. 6, experiment 14), as did a recombination of all five silica gel fractions of JAE (FIG. 6, experiment 15). JAE formulations lacking fractions 1, 3 or 5 remained attractive (FIG. 3, experiments 16, 18, 20), whereas JAE formulations lacking fraction 2 or 4 had no significant behavioural activity (FIG. 6, experiments 17, 19).

Figure 8:
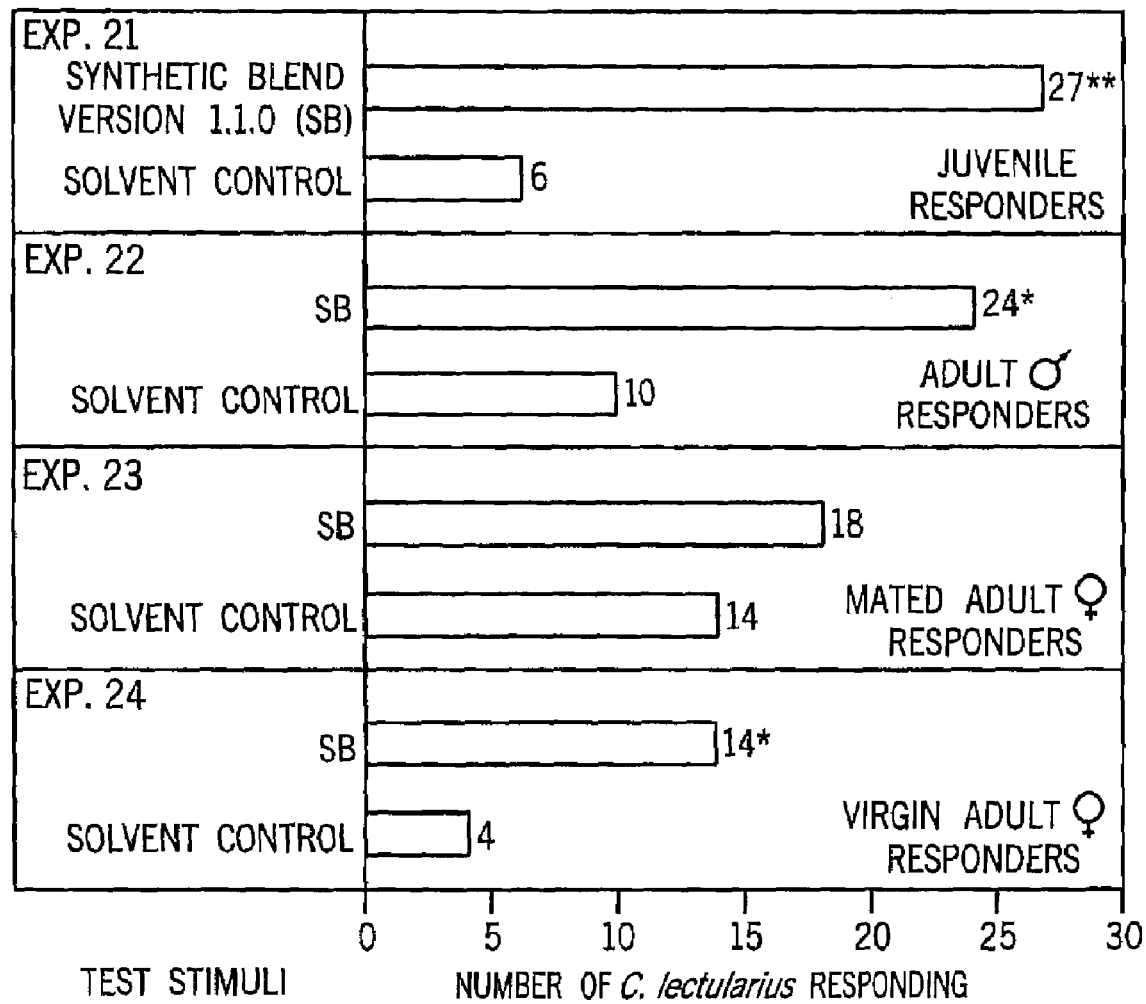
FIG. 8 graphically illustrates the response of juvenile (experiment 21), male (experiment 22), mated female (experiment 23), and virgin female (experiment 24) bedbugs in still-air olfactometers to a synthetic formulation of 14 candidate pheromone components. Number of insects responding to each stimulus is given next to bars. The formulation consisted of two monoterpenes [(+)-limonene, (−)-limonene], three saturated aldehydes [octanal, nonanal, decanal], four unsaturated aldehydes [(E)-2-hexenal, (E)-2-octenal, (E,E)-2,4-octadienal, (E,Z)-2,4-octadienal], one aromatic aldehyde [benzaldehyde], two ketones [sulcatone, geranylacetone], one acetate [benzyl acetate] and one aromatic alcohol [benzyl alcohol]. Aliquots of ~200 BHE were tested for each experiment. The same amount of pentane (10-15 µl) was applied to treatment and control stimuli.
Figure 9:
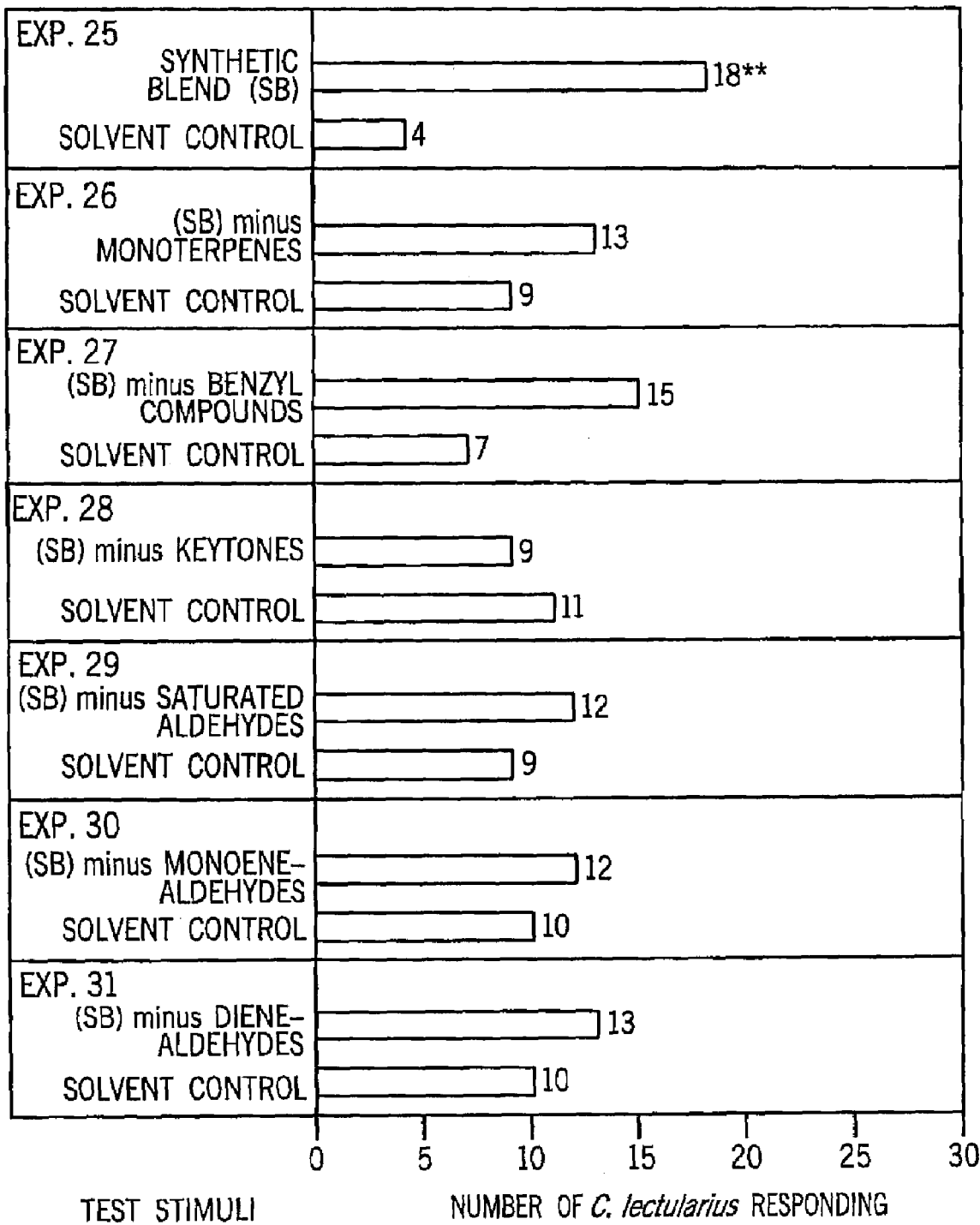
FIG. 9 graphically illustrates the response of juvenile bedbugs in still-air olfactometers to synthetic formulations lacking groups of candidate pheromone components. Number of insects responding to each stimulus is given next to bars. Experiments 25-31 were run in parallel. Aliquots of ~200 BHE were tested for each experiment. The same amount of pentane (15 µl) was applied to treatment and control stimuli.
Figure 10:
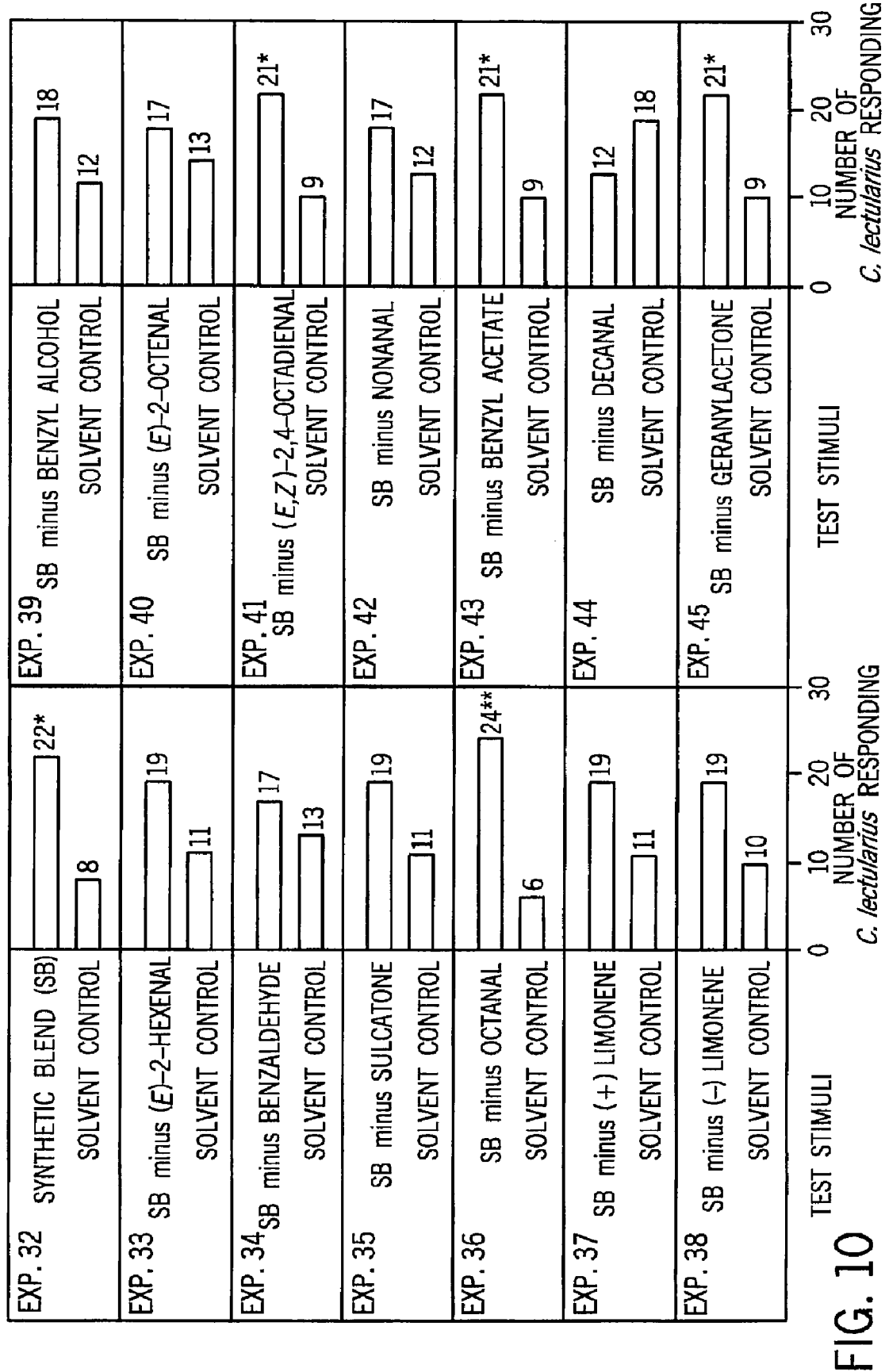
FIG. 10 graphically illustrates the response of juvenile bedbugs in still-air olfactometers to synthetic formulations lacking single candidate pheromone components. Number of insects responding to each stimulus is given next to bars. Experiments 32-45 were run in parallel. Aliquots of ~200 BHE were tested for each experiment. The same amount of pentane (15 µl) was applied to treatment and control stimuli.

A synthetic formulation (SB) of 14 candidate pheromone components tested at ~200 BHE attracted juveniles, males and virgin females (FIG. 8, experiments 21, 22, 24), but failed to elicit a significant response from mated females (FIG. 8, experiment 23). SBs lacking monoterpenes, benzyl-containing compounds, ketones, saturated aldehydes, monoene-aldehydes, or diene-aldehydes were not behaviorally active (FIG. 9, experiments 26-31). SBs lacking either octanal, (E,Z)-2,4-octadienal, benzyl acetate or geranylacetone remained significantly attractive (FIG. 10, experiments 36, 41, 43, 45), whereas SBs lacking either (E)-2-hexenal, benzaldehyde, sulcatone, (+)-limonene, (−)-limonene, benzyl alcohol, (E)-2-octenal, nonanal, or decanal had no behavioural activity (FIG. 9, experiments 33-35, 37-40, 42, 44).

Figure 11:
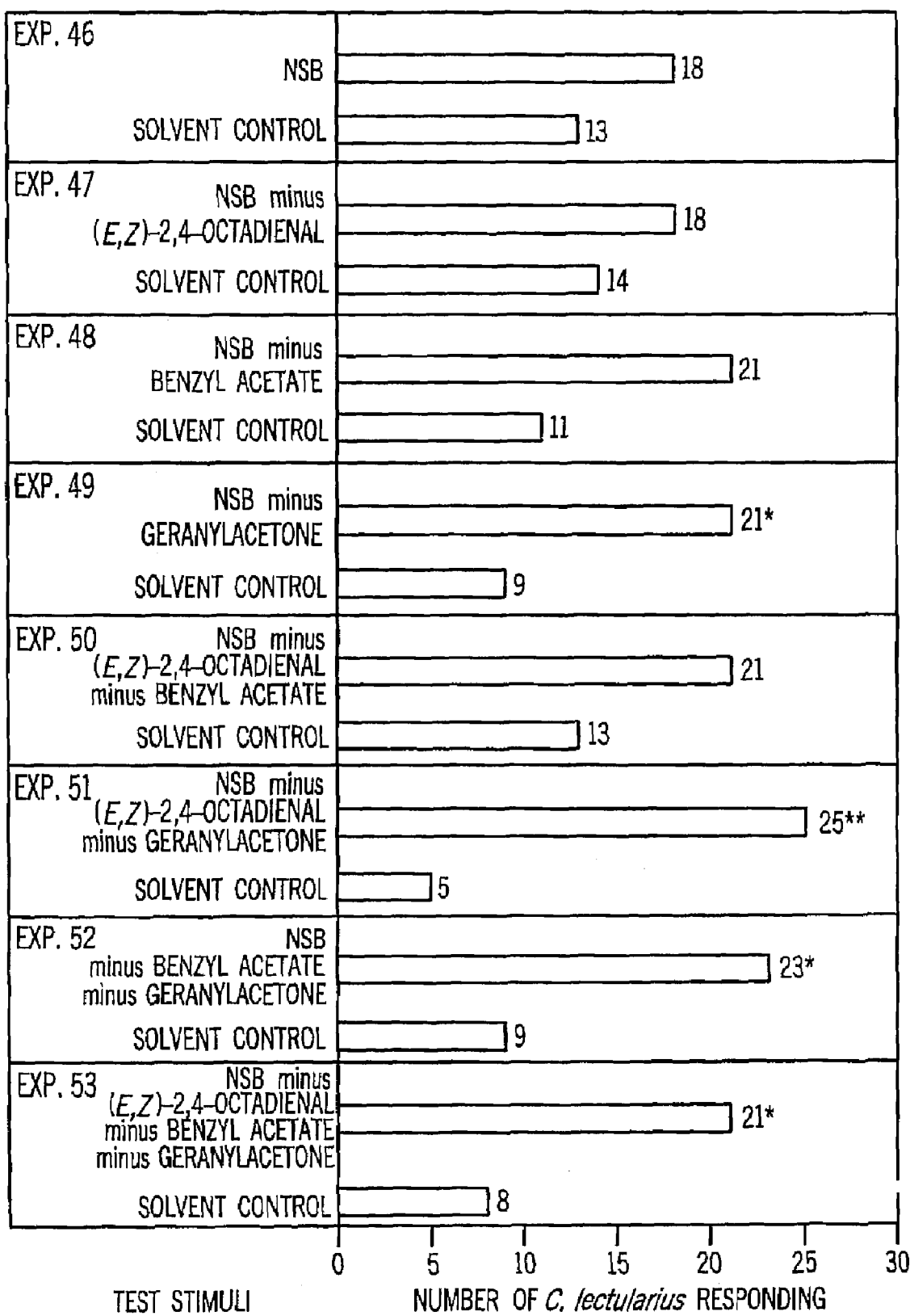
FIG. 11 graphically illustrates the response of juvenile bedbugs in still-air olfactometers to new synthetic formulations (NSB=SB minus octanal) lacking one or more candidate pheromone components. Number of insects responding to each stimulus is given next to bars. NSB consisted of two monoterpenes [(+)-limonene, (−)-limonene], two saturated aldehydes [nonanal, decanal], four unsaturated aldehydes [(E)-2-hexenal, (E)-2-octenal, (E,E)-2,4-octadienal, (E,Z)-2,4-octadienal], one aromatic aldehyde [benzaldehyde], two ketones [sulcatone, geranylacetone], one acetate [benzyl acetate] and one aromatic alcohol [benzyl alcohol]. Experiments 46-53 were run in parallel. Aliquots of ~200 BHE were tested for each experiment. The same amount of pentane (10 µl) was applied to treatment and control stimuli.

A new synthetic formulation (NSB) [SB minus octanal] failed to attract juveniles (FIG. 11, experiment 46) and NSBs lacking (E,Z)-2,4-octadienal, benzyl acetate, or both were not significantly attractive (FIG. 11, experiments 47, 48, 50). All NSBs lacking geranylacetone, including the NSB without the four components octanal, (E,Z)-2,4-octadienal, benzyl acetate and geranylacetone were attractive (FIG. 11, experiments 49, 51-53).

Figure 12:
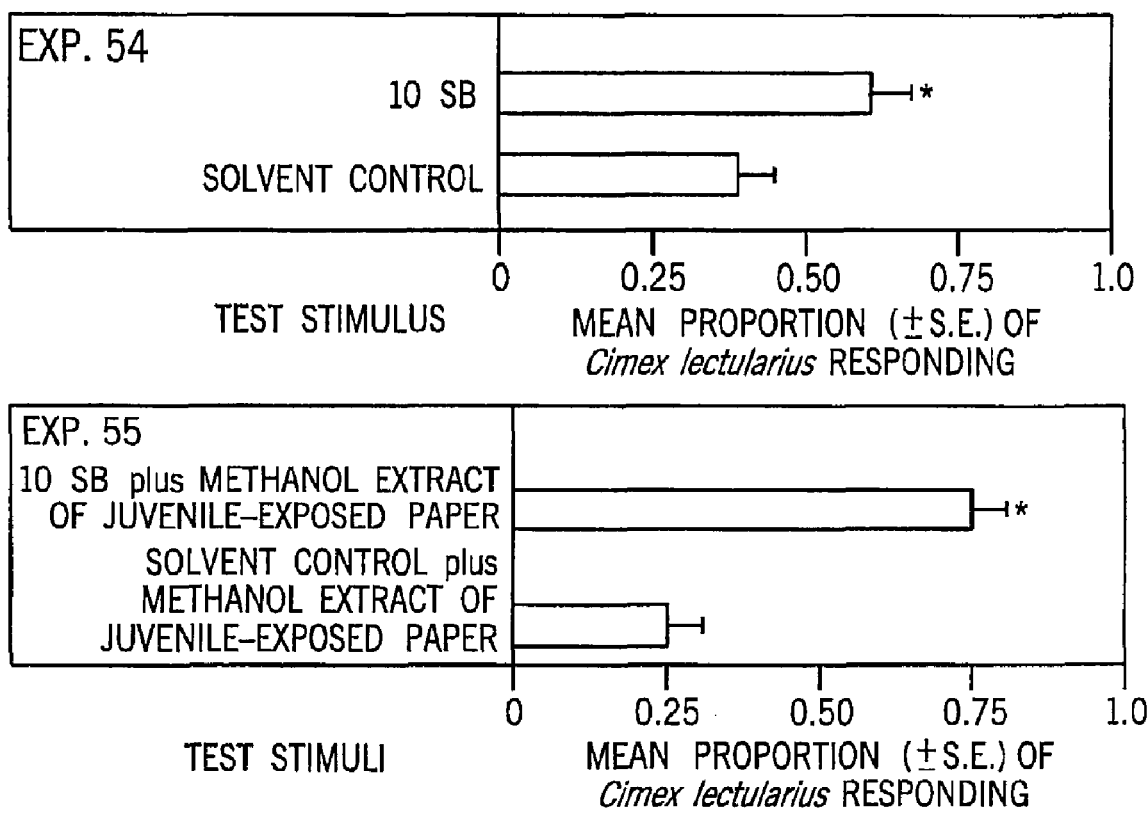
FIG. 12 graphically illustrates mean proportion (±SE) of 10 juvenile bedbugs per replicate (10 replicates) responding in cage olfactometers to a synthetic formulation (experiment 54) or SB in combination with methanol extract of paper exposed to juveniles (experiment 55). SB aliquots of ~2000 BHE were tested for each experiment. The same amount of pentane (50 µl) was applied to treatment and to control stimuli for each experiment. Methanol extract aliquots (100 µl) of 720 CPHE were applied to both treatment and control stimuli for experiment 55.

In cage experiment 54, discs treated with SB at ~2000 BHE attracted significantly more juvenile bedbugs than control discs (FIG. 12). In cage experiment 55, SB tested in combination with methanol extract of juvenile contact pheromone at 720 CPHE attracted a greater proportion of test insects than contact pheromone extract alone (FIG. 12).

Figure 13:
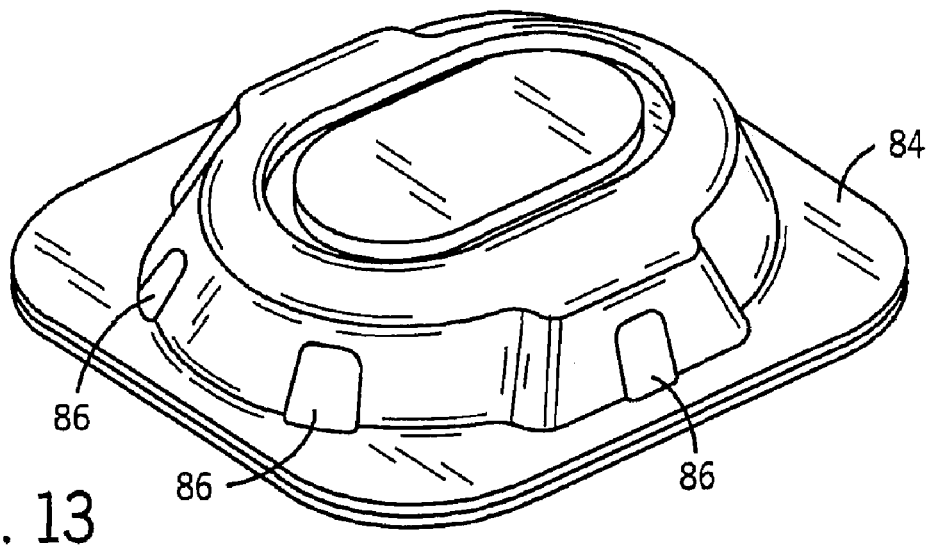
FIG. 13 is a top, frontal perspective view of a trap of the present invention, of the toxic bait type.
Figure 14:
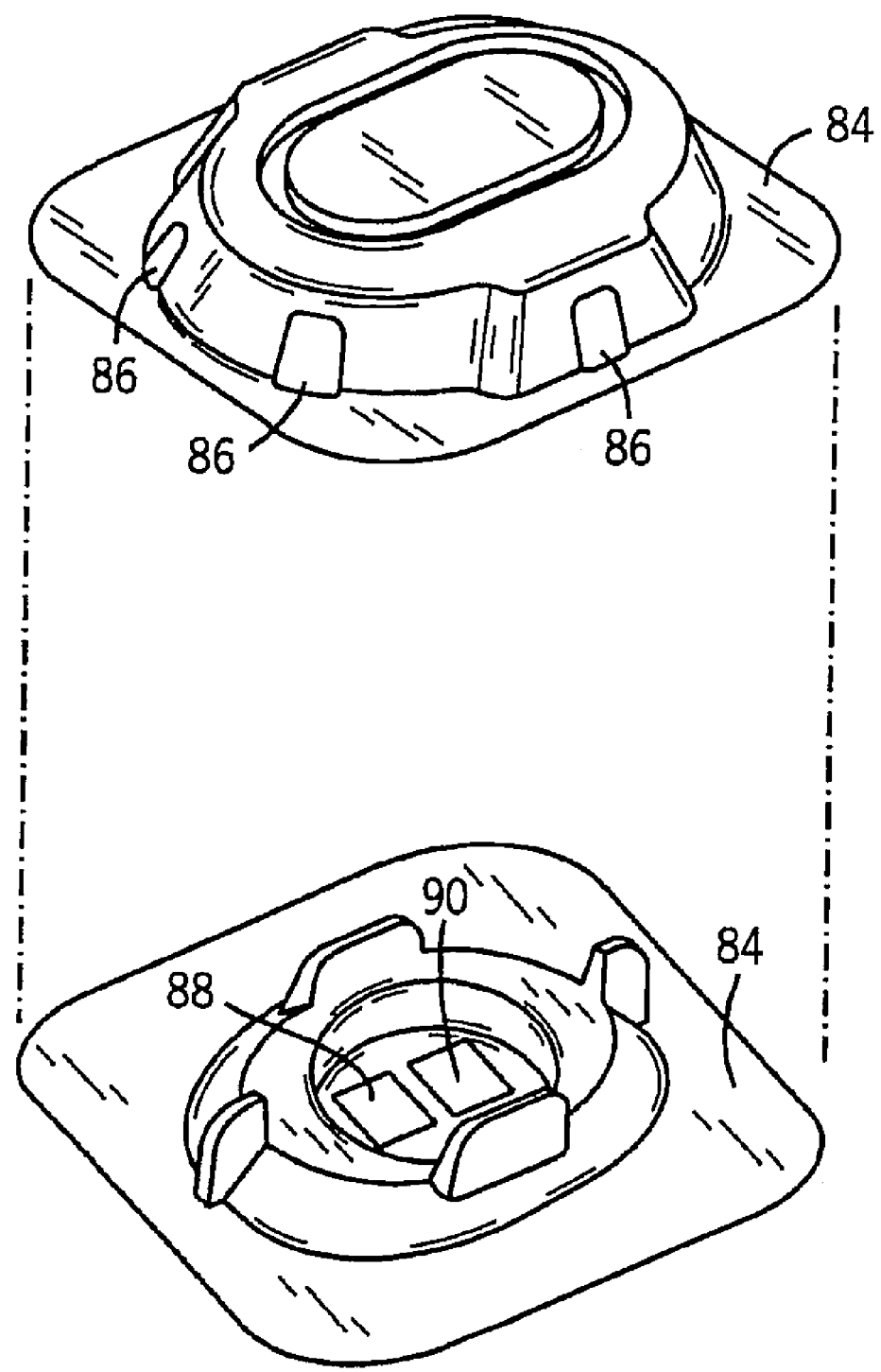
FIG. 14 is an exploded perspective view of the FIG. 13 device.

FIGS. 13 and 14 disclose a bedbug trap which uses a toxic bait to control the insect. Here there is a housing 84 with entryways 86 sized to allow an insect such as a bedbug to enter. A pheromone formulation is positioned within the housing 84 by impregnating a substrate 88 such as paper with it. Preferably, the paper is also impregnated with a contact toxin.

An infrared generator and reflector 90 that emits infrared radiation as discussed above can also be positioned inside the housing 84. Bedbugs are attracted into the housing 84. They then ingest or otherwise come into contact with the toxin, and are thereby controlled. Alternatively, the reflector could be omitted.

A wide variety of toxic pesticides may be suitable for use in connection with the present invention. By way of example, and not limitation, these may include aerosol sprays [e.g. "Pro Aerosol" (pyrethrins, piperonyl butoxide); "Air Guard Konk" (pyrethrins, piperonyl butoxide, n-octyl bicycloheptene dicarboximide); liquid residuals ["Tempo" (cyfluthrin); "Dragnet" (permethrin (55% max. cis/45% min. trans), and dusts ["Ficam" (Bendiocarb); "Drione" (pyrethrins, piperonyl butoxide, amorphous silica gel)].

While a number of embodiments of the present invention have therefore been described, it should be appreciated that there are numerous other embodiments of the invention within the spirit and scope of this disclosure. For example, it is expected that similar results to those found in the experiments on common bedbugs will work on other bedbugs as well. Hence, the invention is not to be limited to just the specific embodiments shown or described.

INDUSTRIAL APPLICABILITY

Provided herein are insect traps and other insect control devices particularly well suited for use in residential locations to control bedbugs, as well as compositions for use therewith and methods for using them.

We claim:

1. A method for attracting a bedbug to a specified location, comprising:
   volatizing a pheromone formulation from a bedbug control device;
   wherein the pheromone formulation comprises nonanal, decanal, (E)-2-hexenal, (E)-2-octenal, (E,E)-2,4-octadienal, benzaldehyde, benzyl alcohol, (+)-limonene, (−)-limonene and sulcatone;
   exposing the bedbug to that pheromone formulation;
   whereby the bedbug is attracted towards the specified location.

2. The method of claim 1, wherein the pheromone formulation also comprises benzyl acetate.

3. The method of claim 1, wherein the pheromone formulation is positioned adjacent to or in a bedbug control device selected from the group consisting of bedbug traps, bedbug baiting stations having a chemical toxic to bedbugs, bedbug feeding stations having a chemical toxic to bedbugs, and bedbug indicator stations.

4. The method of claim 1, wherein the bedbug is a *Cimex lectularius*.

5. The method of claim 1, further comprising generating infrared radiation adjacent the specified location and also exposing the bedbug to that radiation.

6. The method of claim 5, wherein a source of the infrared radiation has an apparent temperature in a range of between 25 degrees Celsius and 45 degrees Celsius when the bedbug is exposed to the infrared radiation.

7. The method of claim 5, wherein the infrared radiation is generated in a manner that attracts the bedbug without heating the bedbug.

8. The method of claim 7, wherein the infrared radiation is reflected off of a mirror prior to reaching the bedbug.

9. The method of claim 5, wherein the bedbug is a *Cimex lectularius* bedbug.

10. The method of claim 5, wherein the infrared radiation is generated from a light emitting diode.

11. A bedbug attractant that is not in contact with a bedbug, the bedbug attractant comprising decanal in a pheromone formulation also comprising at least eight different ingredients selected from the group consisting of nonanal, (E)-2-hexenal, (E)-2-octenal, (E,E)-2,4-octadienal, benzaldehyde, benzyl alcohol, (+)-limonene, (−)-limonene and sulcatone
   the attractant comprising nonanal, decanal, (E)-2-hexenal, (E)-2-octenal, (E,E)-2,4-octadienal, benzaldehyde, benzyl alcohol, (+)-limonene, (−)-limonene and sulcatone.

12. A bedbug control apparatus, comprising:
   a housing;
   a generator positioned adjacent to or in the housing;
   at least one way for the bedbug to access the housing; and
   a pheromonal formulation positioned relative to the generator comprising nonanal, decanal, (E)-2-hexenal, (E)-2-octenal, (E,E)-2,4-octadienal, benzaldehyde, benzyl alcohol, (+)-limonene, (−)-limonene and sulcatone, so that the generator is configured to be able to volatize the pheromonal formulation.

13. The bedbug control apparatus of claim 12, wherein the bedbug control apparatus further comprises a toxic agent suitable to kill entering bedbugs.

14. The bedbug control apparatus of claim 12, wherein the bedbug control apparatus further comprises a generator for generating infrared radiation.

15. The bedbug control apparatus of claim 12, wherein the bedbug is a *Cimex lectularius* bedbug.

* * * * *